United States Patent
Shin

(10) Patent No.: US 9,932,270 B2
(45) Date of Patent: Apr. 3, 2018

(54) FUNCTIONAL ECOSTONE AND METHOD FOR MANUFACTURING SAME

(71) Applicant: YOUNG WOO INDUSTRY, Jeonju-si, Jeollabuk-do (KR)

(72) Inventor: Jae Moo Shin, Jeonju-si (KR)

(73) Assignee: INECO INC., Jeonju-si, Jeollabuk-Do (KR)

( * ) Notice: Subject to any disclaimer, the term of this patent is extended or adjusted under 35 U.S.C. 154(b) by 0 days.

(21) Appl. No.: 15/301,670

(22) PCT Filed: Jun. 18, 2015

(86) PCT No.: PCT/KR2015/006177
§ 371 (c)(1),
(2) Date: Oct. 3, 2016

(87) PCT Pub. No.: WO2016/003093
PCT Pub. Date: Jan. 7, 2016

(65) Prior Publication Data
US 2017/0183261 A1    Jun. 29, 2017

(30) Foreign Application Priority Data

Jul. 4, 2014    (KR) .......................... 10-2014-0083887

(51) Int. Cl.
*C04B 28/14* (2006.01)
*B28B 1/24* (2006.01)
(Continued)

(52) U.S. Cl.
CPC .............. *C04B 28/14* (2013.01); *A01N 65/00* (2013.01); *A01N 65/08* (2013.01); *B28B 1/24* (2013.01);
(Continued)

(58) Field of Classification Search
None
See application file for complete search history.

(56) References Cited

U.S. PATENT DOCUMENTS 5,482,543 A  *  1/1996  Bleve ..................... C04B 24/14
                                                    106/124.2

FOREIGN PATENT DOCUMENTS

CN         103556542 A   *   2/2014
CN         104150852 A   *  11/2014
(Continued)

OTHER PUBLICATIONS

Ma et al., "Naturally Occurring Charcoal: A Trace Element Sink?" In: Roach I.C. ed. 2005. Regolith 2005—Ten Years of CRC LEME. CRC LEME, pp. 219-220.*

(Continued)

*Primary Examiner* — David Sample
(74) *Attorney, Agent, or Firm* — Novick, Kim & Lee, PLLC; Jae Youn Kim

(57) ABSTRACT

Disclosed are a functional Ecostone and a method for manufacturing the same, wherein the functional Ecostone is characterized in that, on the basis of 100 parts by weight of a raw material formed by mixing 30-60 wt % of gypsum, 20-40 wt % of calcium carbonate, and 10-30 wt % of water, 1-30 parts by weight of a rose geranium extract, 2-10 parts by weight of basalt fibers, 2-10 parts by weight of mulberry fibers, 1-30 parts by weight of phytoncide, 1-30 parts by weight of ocher, and 1-30 parts by weight of charcoal are mixed.

3 Claims, 1 Drawing Sheet

Raw material forming step

↓

Mixture forming step

↓

Molding and demolding step

(51) Int. Cl.
*C04B 14/46* (2006.01)
*C04B 18/24* (2006.01)
*A01N 65/08* (2009.01)
*A01N 65/00* (2009.01)

(52) U.S. Cl.
CPC ........ *C04B 14/4668* (2013.01); *C04B 18/248* (2013.01)

(56) References Cited

FOREIGN PATENT DOCUMENTS

| | | |
|---|---|---|
| KR | 10-1998-0018145 A | 6/1998 |
| KR | 10-2004-0004773 A | 1/2004 |
| KR | 10-2004-0004806 A | 1/2004 |
| KR | 100467204 B1 | 1/2005 |
| KR | 10-0611709 B1 | 8/2006 |
| KR | 10-2012-0043192 A | 5/2012 |

OTHER PUBLICATIONS

Hawley's Condensed Chemical Dictionary, definition of Ocher, Limestone and Gyspum, Mar. 15, 2007.*
Miriam Webster Dictionary, https://www.merriam-webster.com/medical/phytoncide; visited Sep. 26, 2017.*

* cited by examiner

Raw material forming step
Mixture forming step
Molding and demolding step

US 9,932,270 B2

FUNCTIONAL ECOSTONE AND METHOD FOR MANUFACTURING SAME

TECHNICAL FIELD

The present invention relates to a functional ecostone and a method for manufacturing the same, and more particularly, to a functional ecostone and a method for manufacturing the same, in which on the basis of 100 parts by weight of a raw material formed by mixing 30 to 60 wt % of gypsum, 20 to 40 wt % of calcium carbonate, and 10 to 30 wt % of water, 1 to 30 parts by weight of a rose geranium extract, 2 to 10 parts by weight of basalt fibers, 2 to 10 parts by weight of mulberry fibers, 1 to 30 parts by weight of phytoncide, 1 to 30 parts by weight of ocher, and 1 to 30 parts by weight of charcoal are mixed.

RELATED ART

Generally, concrete is a complex material made by mixing cement with sand, gravel, and water and has large resistance to water as compared with woods or steels and is easily processed with various types and dimensions, and is a construction material which is most widely used on the earth.

Recently, as recognition for surrounding environments is improved due to an increase in national income, there are a lot of investment to improve the city appearance by applying various colors and designs departing from existing standardized and uniformized frameworks of thoroughly gray of various civil engineering and building structures. As public interests and demands for various infrastructures and sports and leisure for social welfare and daily life and culture are rapidly increased, a paint demand market such as various colors and shapes of pavements, bicycle paths, bus lanes, coastal embankments and facilities, and walking path facilities is rapidly increasing.

As such, the needs of consumers for the aesthetics of concrete products are rapidly changing, but there is a limitation to satisfy the needs by the existing products.

Meanwhile, in houses or buildings, the interior is performed by attaching and installing wallpapers or tiles with patterns on the surface of a wall or a partition wall and "a sick building syndrome" by formaldehyde generated from wallpapers and flooring materials using cements and various adhesives has been issued. As a result, as the interest in building materials using natural components is increased, various products such as flat stones, bricks, and mortar using ocher of which the efficacy is well-known have been developed.

DISCLOSURE

Technical Problem

The present invention is directed to provide a functional ecostone having advantages of preventing intrusion of harmful insects such as mosquito, having excellent strength and sound absorption power, preventing various environmental diseases having a moisture control function, and having an excellent deodorizing effect.

Technical Solution

One aspect of the present invention provides a functional ecostone in which on the basis of 100 parts by weight of a raw material formed by mixing 30 to 60 wt % of gypsum, 20 to 40 wt % of calcium carbonate, and 10 to 30 wt % of water, 1 to 30 parts by weight of a rose geranium extract, 2 to 10 parts by weight of basalt fibers, 2 to 10 parts by weight of mulberry fibers, 1 to 30 parts by weight of phytoncide, 1 to 30 parts by weight of ocher, and 1 to 30 parts by weight of charcoal are mixed.

Further, the surface of the ecostone may be nanosilver-coated.

Another aspect of the present invention provides a method for manufacturing a functional ecostone comprising: forming a raw material by mixing 30 to 60 wt % of gypsum, 20 to 40 wt % of calcium carbonate, and 10 to 30 wt % of water; forming a mixture by mixing 1 to 30 parts by weight of a rose geranium extract, 2 to 10 parts by weight of basalt fibers, 2 to 10 parts by weight of mulberry fibers, 1 to 30 parts by weight of phytoncide, 1 to 30 parts by weight of ocher, and 1 to 30 parts by weight of charcoal on the basis of 100 parts by weight of the raw material; and injecting the mixture into a molding frame or a mold and demolding the mixture.

Advantageous Effects

According to the present invention, the ecostone is formed by mixing the rose geranium extract, the basalt fibers, the mulberry fibers, the phytoncide, the ocher, and the charcoal, thereby preventing intrusion of harmful insects, having excellent strength and sound absorption power, and having a moisture control function and an excellent deodorizing effect while preventing occurrence of a sick building syndrome, emitting far-infrared radiation, and maintaining moisture control and anti-condensation effects which are advantages of a general ecostone.

DESCRIPTION OF DRAWINGS

FIG. 1 is a process diagram for manufacturing a functional ecostone according to the present invention.

MODES OF THE INVENTION

Hereinafter, a functional ecostone and a method for manufacturing the same according to the present invention will be described.

The ecostone has advantages of preventing a sick building syndrome from occurring by formaldehyde generated in wallpapers, flooding materials, and the like using various adhesives, emitting far-infrared radiation, and having moisture control and anti-condensation effects, antifungal and antibacterial effects, and electromagnetic removal and an odor removal effects.

The present invention has a technical feature of preventing intrusion of harmful insects, improving strength and sound absorption power, preventing environmental diseases, and adding a deodorizing function while the advantages of the general ecostone as it is by mixing a rose geranium extract, basalt fibers, mulberry fibers, phytoncide, ocher, and charcoal in a raw material formed by mixing gypsum, calcium carbonate, and water.

First, in the functional ecostone according to the present invention, the raw material is formed by mixing gypsum, calcium carbonate, and water.

The raw material is characterized in that 30 to 60 wt % of gypsum, 20 to 40 wt % of calcium carbonate, and 10 to 30 wt % of water are mixed.

Herein, the reason why 10 to 30 wt % of water is mixed on the basis of 100 parts by weight of the raw material is that a hardening speed varies according to a mixed amount of water. The reason for adjusting the hardening speed is that an operation of removing remaining bubbles in the molds after sequentially pouring the mixture formed by the raw material into a plurality of molds and then is required, and when the hardening speed is too fast, the bubbles can not be removed, and thus defects of the product occur.

Next, the functional ecostone according to the present invention is characterized in that the rose geranium extract, the basalt fibers, the mulberry fibers, the phytoncide, the ocher, and the charcoal are mixed in the raw material.

First, the rose geranium extract belongs to a pelargonium species, emits a pennyroyal mint perfume and a citronella perfume, and has effects of efficiently preventing and eradicating various harmful insects including mosquitoes from being approached through an insect repellent perfume characteristic having the perfumes.

The rose geranium extract may be extracted through various methods and for example, may be obtained by isolating and removing solids after separating and pressing leaves from rose geranium.

The rose geranium extract is mixed with 1 to 30 parts by weight on the basis of 100 parts by weight of the raw material. When the rose geranium extract is mixed with less than 1 part by weight, effects of blocking and eradicating mosquitoes and harmful insects may be deteriorated due to the lack of the content of ingredients. Further, the rose geranium extract has a feature of emitting a rose perfume to obtain effects as a flavoring agent when a large amount of rose geranium extract is mixed within a reference value range.

The basalt fibers are to fiberize natural basalt and have excellent tensile strength to have characteristics of low density, low thermal expansion, heat resistance, chemical stability, self-lubricating, elasticity, and sound absorption, and are strong in the fire and increase the tensile strength to compensate for a disadvantage of being easily broken.

The basalt fibers have more excellent property and eco-friendly than existing glass fibers to be suitable for interior finishing materials.

The basalt fibers are mixed with 2 to 10 parts by weight on the basis of 100 parts by weight of the raw material.

When the basalt fibers are mixed with less than 2 parts by weight, there is a problem in that heat resistance and strength are deteriorated, and when the basalt fibers are greater than 10 parts by weight, there is a problem in that the ecostone is not uniformly formed due to excessive aggregation. That is, the ecostone used for the interior puts emphasis on aesthetics, and when the basalt fibers are contained with a reference value or greater and thus excessive aggregation occurs, the ecostone is not uniformly formed and thus it is difficult to manufacture the product.

The mulberry fibers as a raw material of hangi have excellent formability and eco-friendly to improve an interior function of mimicking the feeling of the hangi, enhance humidity control capability, and improve resistance of environmental skin diseases such as atopy.

The mulberry fibers are mixed with 2 to 10 parts by weight on the basis of 100 parts by weight of the raw material. When the mulberry fibers are mixed with less than 2 parts by weight, there is a problem in that the humidity control capability is deteriorated, and when the mulberry fibers are greater than 10 parts by weight, there is a problem in that the ecostone is not uniformly formed due to excessive aggregation like the basalt fibers.

The phytoncide has effects of stress relaxation, improvement of an immune function, central nervous stability, deodorization, and the like as well as an anti-bacterial effect as natural anti-bacterial materials radiated for resisting microorganisms or pathogens around plants to be used for flavoring agents, atopic treating agents, harmful gas removers according to a sick building syndrome, and the like.

The phytoncide is mixed with 1 to 30 parts by weight on the basis of 100 parts by weight of the raw material. When the phytoncide is mixed with less than 1 part by weight, there are disadvantages such as anti-bacterial degradation, stress relaxation function degradation, immune function degradation, deodorization function degradation, and the like.

The ocher blocks various harmful materials that occur in living spaces and has characteristics of deodorization such as decontaminating ability, degradation ability, dehumidifying ability, and moisturizing ability, far-infrared radiation including purification, and incombustible materials. An enzyme element has a function of four kinds of enzyme elements of katalase, diphenol oxydase, saccharase, and protease.

The katalase serves to remove hydrogen peroxide as a toxin. The toxin generated in the metabolic process in the human body causes the aging process and the katalase prevents the aging process caused when lipoperoxide as an endotoxin is neutralized or diluted by strong absorption of the soil.

The diphenol oxydase serves to catalyze the oxidation reaction which occurs by using molecular oxygen. The diphenol oxydase is required to obtain energy required for synthesis of living or biological components and serves to perform oxidation and reduction of various organic/inorganic compounds in the body.

The saccharase is an enzyme of making glucose and fructose by hydrolyzing sucrose, and the protease serves to hydrolyze a protein to amino acids when nitrogen in the protein is mineralized. Other bad cells such as unnecessary cancer beside the immunity may be decomposed and broken in an instant.

The ocher having the enzymes has effects of generating far-infrared rays to promote a flow of blood, promoting the perspiration, excreting waste accumulated in the living body, and emitting heavy metals and has advantages of preventing the growth of fungi and having an excellent dehumidifying effect in addition to anti-bacterial and anti-insect effects.

Further, the ocher has an air pollution purification function as a cause of chemical and electro-radioactive materials and has advantages of purifying harmful materials such as formalin, removing cigarette smoke or odor, blocking harmful electromagnetic waves, filtering, and adjusting humidity.

The present invention may strength a unique advantage of the ocher by mixing the ocher having various effects in the raw material to maximize the function and to this end, the ocher is mixed with 1 to 30 parts by weight on the basis of 100 parts by weight of the raw material. When the ocher is mixed with less than 1 part by weight, the ocher may exhibit various effects due to the lack of the component content.

Next, the charcoal has effects of purifying air, releasing a large amount of anions to affect the parasympathetic nerve and stabilize feelings, and relaxing the tension of the body and promotes blood circulation by emitting far-infrared rays.

Further, the charcoal has excellent absorption, conductivity, and storage of electricity to block electromagnetic waves and absorb the odor, purifies air and adjusts the humidity, has anti-bacterial and detoxification functions, prevents intrusion of harmful insects, and helps in deep sleep and fatigue recovery to charge the energy.

The present invention may more maximize functions such as air purification, flavoring and deodorizing effects, prevention of harmful insects, absorption of electromagnetic waves, an antibacterial effect, deep sleep and fatigue recovery functions, energy charging, emission of anions, and humidity controlling by forming the ecostone by mixing 1 to 30 parts by weight of the charcoal having the functions on the basis of 100 parts by weight of the raw material.

When the charcoal is mixed in the raw material, if the charcoal is mixed with less than 1 part by weight, the charcoal may not exhibit various effects due to the lack of the component content.

The functional ecostone according to the present invention is manufactured by forming a raw material by mixing gypsum, calcium carbonate, and water, and forming a mixture by mixing a rose geranium extract, basalt fibers, mulberry fibers, phytoncide, ocher, and charcoal in the raw material, and injecting the mixture in a molding frame or a mold and molding the mixture.

Next, the functional ecostone according to the present invention is characterized in that the surface is nanosilver-coated.

From old times, it is known that silver has a proliferation inhibition effect and a sterilizing function to approximately 650 types of germs, bacteria, and fungi, and a nanosilver coating process has an advantage of extending the lifespan of the products by improving durability and abrasion resistance in addition to an excellent anti-bacterial function, deodorization, and water resistance.

Accordingly, the present invention has advantages of increasing effects such as an anti-bacterial effect, deodorization, and water resistance by coating nanosilver on the surface of the ecostone and reducing the burden for the maintenance or repurchase of the product by extending the lifespan of the product.

The present invention configured above can prevent intrusion of harmful insects such as mosquitoes, have excellent strength and sound absorption, preventing various environmental diseases due to a humidity control function, and have an excellent deodorization effect.

The invention claimed is:

1. A molded functional ecostone for building materials, the functional ecostone comprising: 1 to 30 parts by weight of a rose geranium extract, 2 to 10 parts by weight of basalt fibers, 2 to 10 parts by weight of mulberry fibers, 1 to 30 parts by weight of phytoncide, 1 to 30 parts by weight of ocher, and 1 to 30 parts by weight of charcoal, on a basis of 100 parts by weight of a raw material formed by mixing 30 to 60 wt % of gypsum, 20 to 40 wt % of calcium carbonate, and 10 to 30 wt % of water.

2. The functional ecostone of claim 1, wherein a surface of the ecostone is nanosilver-coated.

3. A method for manufacturing a functional ecostone, the method comprising:
    forming a raw material by mixing 30 to 60 wt % of gypsum, 20 to 40 wt % of calcium carbonate, and 10 to 30 wt % of water;
    forming a mixture by mixing 1 to 30 parts by weight of a rose geranium extract, 2 to 10 parts by weight of basalt fibers, 2 to 10 parts by weight of mulberry fibers, 1 to 30 parts by weight of phytoncide, 1 to 30 parts by weight of ocher, and 1 to 30 parts by weight of charcoal on a basis of 100 parts by weight of the raw material; and
    injecting the mixture into a molding frame or a mold and then demolding the mixture.

* * * * *